US012544761B2

(12) United States Patent
Tanabe

(10) Patent No.: US 12,544,761 B2
(45) Date of Patent: Feb. 10, 2026

(54) MICROFLUIDIC DEVICE AND NUCLEIC ACID AMPLIFICATION METHOD

(71) Applicant: Brady Worldwide, Inc., Milwaukee, WI (US)

(72) Inventor: Hideki Tanabe, Osaka (JP)

(73) Assignee: BRADY WORLDWIDE, INC., Milwaukee, WI (US)

( * ) Notice: Subject to any disclaimer, the term of this patent is extended or adjusted under 35 U.S.C. 154(b) by 1035 days.

(21) Appl. No.: 17/522,880

(22) Filed: Nov. 9, 2021

(65) Prior Publication Data

US 2022/0193683 A1 Jun. 23, 2022

(30) Foreign Application Priority Data

Dec. 22, 2020 (JP) ................................ 2020-212728

(51) Int. Cl.
*B01L 7/00* (2006.01)
*B01L 3/00* (2006.01)
*C12Q 1/6848* (2018.01)

(52) U.S. Cl.
CPC ......... *B01L 7/525* (2013.01); *B01L 3/502715* (2013.01); *B01L 3/502746* (2013.01); *C12Q 1/6848* (2013.01); *B01L 2300/042* (2013.01); *B01L 2300/0663* (2013.01); *B01L 2300/1805* (2013.01)

(58) Field of Classification Search
CPC ............... B01L 7/525; B01L 3/502715; B01L 3/502746; B01L 2300/042; B01L 2300/0663; B01L 2300/1805; C12Q 1/6848
See application file for complete search history.

(56) References Cited

U.S. PATENT DOCUMENTS

| | | | |
|---|---|---|---|
| 7,235,406 B1 | 6/2007 | Woudenberg et al. | |
| 8,246,803 B2 | 8/2012 | Yamazaki et al. | |
| 10,994,275 B2 | 5/2021 | Pallas et al. | |
| 11,654,436 B2 | 5/2023 | Rausch et al. | |
| 2005/0221373 A1* | 10/2005 | Enzelberger ........ | B01L 3/50273 435/6.19 |
| 2007/0084279 A1 | 4/2007 | Huang et al. | |
| 2007/0104615 A1 | 5/2007 | Hanafusa et al. | |

(Continued)

FOREIGN PATENT DOCUMENTS

| | | |
|---|---|---|
| AU | 727296 B2 | 12/2000 |
| EP | 4454758 A1 | 10/2024 |

(Continued)

*Primary Examiner* — Jill A Warden
*Assistant Examiner* — Alex Ramirez
(74) *Attorney, Agent, or Firm* — Brianna Schonenberg

(57) ABSTRACT

A microfluidic device for amplifying a nucleic acid includes a cartridge and a control part. The cartridge includes a tank part and a plurality of first chambers. The control part is configured to control execution of a thermal cycle, count a number of repetitions of the thermal cycle for each of the first chambers and store a count value, acquire a fluorescence intensity of each of the first chambers for each thermal cycle, and reset the count value of a defective chamber of which the fluorescence intensity is not within a predetermined range, discharge the solution from the defective chamber, and fill the defective chamber with a new solution from the tank part.

12 Claims, 13 Drawing Sheets

(56) References Cited

U.S. PATENT DOCUMENTS

| | | | |
|---|---|---|---|
| 2008/0110756 | A1 | 5/2008 | Yamazaki et al. |
| 2009/0004729 | A1 | 1/2009 | Moriwaki et al. |
| 2009/0087344 | A1 | 4/2009 | Kajiyama et al. |
| 2011/0183378 | A1 | 7/2011 | Takagi et al. |
| 2012/0058519 | A1 | 3/2012 | Knight et al. |
| 2014/0091208 | A1 | 4/2014 | Kai |
| 2014/0141527 | A1 | 5/2014 | Ding et al. |
| 2016/0288119 | A1 | 10/2016 | Asogawa et al. |
| 2016/0290962 | A1 | 10/2016 | Asogawa et al. |
| 2016/0310948 | A1 | 10/2016 | Nowakowski et al. |
| 2016/0375438 | A1* | 12/2016 | Marcy .................... B01L 9/527 506/39 |
| 2017/0051335 | A1 | 2/2017 | Nazareth et al. |
| 2017/0056879 | A1 | 3/2017 | Nazareth et al. |
| 2017/0225171 | A1 | 8/2017 | Nazareth et al. |
| 2017/0232441 | A1 | 8/2017 | Nazareth et al. |
| 2018/0002737 | A1 | 1/2018 | Uehara |
| 2019/0250102 | A1 | 8/2019 | Iizuka et al. |
| 2019/0316963 | A1 | 10/2019 | Ishida et al. |
| 2020/0061620 | A1 | 2/2020 | Anderson et al. |
| 2020/0398282 | A1 | 12/2020 | Sato et al. |
| 2021/0008547 | A1 | 1/2021 | Ely et al. |
| 2021/0023565 | A1 | 1/2021 | Usami et al. |
| 2021/0069705 | A1 | 3/2021 | Nielsen et al. |
| 2021/0276016 | A1 | 9/2021 | Buckland et al. |
| 2022/0193683 | A1 | 6/2022 | Tanabe |
| 2022/0205018 | A1 | 6/2022 | Li et al. |
| 2024/0307869 | A1 | 9/2024 | Cho et al. |

FOREIGN PATENT DOCUMENTS

| | | | |
|---|---|---|---|
| JP | H11311616 | A | 11/1999 |
| JP | 2000511435 | | 9/2000 |
| JP | 2004069499 | A | 3/2004 |
| JP | 2007033181 | A | 2/2007 |
| JP | 2007047110 | A | 2/2007 |
| JP | 2007113996 | A | 5/2007 |
| JP | 2007315772 | A | 12/2007 |
| JP | 2008164434 | A | 7/2008 |
| JP | 2010139491 | A | 6/2010 |
| JP | 4597711 | B2 | 12/2010 |
| JP | 4720419 | B2 | 7/2011 |
| JP | 4909744 | B2 | 4/2012 |
| JP | 4969061 | B2 | 7/2012 |
| JP | 5219415 | B2 | 6/2013 |
| JP | 2014153242 | A | 8/2016 |
| JP | 2016165247 | A | 9/2016 |
| JP | 6047448 | B2 | 12/2016 |
| JP | 2017510796 | | 4/2017 |
| JP | 6247064 | B2 | 12/2017 |
| JP | 2018512882 | | 5/2018 |
| JP | 6350349 | B2 | 7/2018 |
| JP | 2025017397 | A | 2/2025 |
| KR | 102001150 | B1 | 7/2019 |
| WO | 2005/064325 | A2 | 7/2005 |
| WO | 2015041282 | A1 | 3/2015 |

* cited by examiner

MICROFLUIDIC DEVICE AND NUCLEIC ACID AMPLIFICATION METHOD

CROSS-REFERENCE TO RELATED APPLICATION

This application claims the priority benefit of Japan application serial no. 2020-212728, filed on Dec. 22, 2020. The entirety of the above-mentioned patent application is hereby incorporated by reference herein and made a part of this specification.

BACKGROUND

Technical Field

The disclosure relates to a microfluidic device and a nucleic acid amplification method.

Description of Related Art

Polymerase chain reaction (PCR) is one of the methods for amplifying nucleic acids. PCR is a method in which a fragment of DNA specified as a test target is mixed with a suitable primer and a specific chemical such as an enzyme, and a thermal cycle including heating and cooling is repeated in a PCR tester to amplify a specific region of the target DNA sample. Recently, there have also been methods called quantitative PCR (qPCR) and real-time PCR, which analyze the reaction in the process of exponentially increasing DNA by directly observing fluorescence. Such devices and methods for PCR are disclosed, for example, in Patent Document 1 (Japanese Patent Application Laid-Open No. 2000-511435), Patent Document 2 (Japanese Patent Application Laid-Open No. 2018-512882), and Patent Document 3 (Japanese Patent Application Laid-Open No. 2017-510796).

However, according to the related art, in qPCR, when the starting material is defective, for example, when the starting material contains less DNA fragment as the test target than the expected value, compared to the case in which the starting material is as expected, the fluorescence intensity with respect to DNA amplification is weakened, the desired result cannot be obtained, and there is adverse effect on the result. The adverse effect includes, for example, a problem that the amount of DNA fragment that should have been obtained cannot be obtained.

In addition to such a quantitative defect of DNA fragment as the test target, the defect of the starting material may also cause a qualitative defect. The qualitative defect includes, for example, a case in which a DNA fragment at a site different from the assumed DNA fragment is included. Similarly, in this case, there is a problem that a DNA fragment that should have been obtained cannot be obtained.

SUMMARY

A microfluidic device according to an aspect of the disclosure is a microfluidic device for amplifying a nucleic acid and includes a cartridge (1) storing a solution (30) containing the nucleic acid, and a control part (14) controlling the cartridge. The cartridge (1) includes a tank part (15) storing the solution (30), and a plurality of first chambers (21) holding the solution (30) from the tank part (15). The control part (14) is configured to: control execution of a thermal cycle which changes a temperature of the first chambers (21); count a number of repetitions of the thermal cycle for each of the first chambers and store a count value; acquire a fluorescence intensity of each of the first chambers for each thermal cycle; determine whether the acquired fluorescence intensity of each of the first chambers (21) is within a predetermined range defined in advance for each number of repetitions; determine the first chamber (21) to be a defective chamber when it is determined that the fluorescence intensity is not within the predetermined range; and reset the count value of the defective chamber, discharge the solution from the defective chamber, and fill the defective chamber with a new solution from the tank part.

Accordingly, it is possible to reduce the adverse effect when a quantitative defect or a qualitative defect is present in the starting material contained in the solution held in the first chamber (21). In other words, if a quantitative defect or a qualitative defect is present in the starting material, the control part (14) determines the defective chamber and replaces the solution of the defective chamber with the new solution. That is, the first chamber (21) in which a quantitative defect or a qualitative defect is present in the starting material starts a new thermal cycle with the new solution. Therefore, among the plurality of first chambers (21), the first chambers that have adverse effect can be eliminated or reduced.

For example, the cartridge (1) may include a plurality of first heaters (24) corresponding to the first chambers (21).

Accordingly, since one first heater (24) corresponds to one first chamber (21), in the thermal cycle, the time required for heating the first chamber (21) to the target temperature can be shortened, and the total time required for the thermal cycle can be shortened.

For example, the cartridge (1) may include a plurality of flow path parts (20) connecting the tank part (15) and the first chambers (21). Each of the first chambers (21) may include a first opening (**21*b*) connected to the flow path part (20), and a second opening (21*a*) for discharging the solution held in the first chamber (21). The control part (14) may generate a bubble in the solution in the defective chamber by the first heater (24) corresponding to the defective chamber, discharge the solution of the defective chamber from the second opening by generation of the bubble, and fill the new solution to the defective chamber from the tank part (15) via the flow path part (20) and the first opening (21*a***).

Accordingly, the set of the first heater (24) and the first chamber (21) may serve both of the following two functions. One is to heat the solution of the corresponding first chamber (21) in the thermal cycle. The other is to discharge the solution of the defective chamber and fill the defective chamber with the new solution.

For example, the cartridge (1) may include a plurality of first temperature sensors (25) corresponding to the first chambers (21). The control part (14) may acquire data indicating a temperature from the first temperature sensors (25) in the thermal cycle and manage a temperature of each of the first chambers (21).

Accordingly, the speed and accuracy of temperature control in the thermal cycle can be improved for each of the first chambers (21).

For example, the cartridge (1) may include a thermal head part (16). The thermal head part (16) may include a semiconductor substrate (17) and a head film (18) bonded to the semiconductor substrate (17). The semiconductor substrate (17) may include the first heater (24) and the flow path part (20). The first chamber (21) and the flow path part (20) may be formed as a gap formed by bonding the semiconductor substrate (17) and the head film (18) together.

Accordingly, since the cartridge (1) has the same configuration as a cartridge of a thermal inkjet printer, the manufacturing cost can be reduced and the solution can be easily discharged and filled in the first chamber (21) at the order of picolitre to microliter.

For example, the semiconductor substrate (17) may include a substrate heater (23).

Accordingly, since the first chambers (21) may also be heated from the periphery by heating the semiconductor substrate (17), in the thermal cycle, the time required for heating the solution to the target temperature can be shortened, and the total time required for the thermal cycle can be shortened.

For example, the cartridge (1) may include a plurality of second chambers (22), and a plurality of second heaters (26) corresponding to the second chambers (22). Each of the second chambers (22) may be located in the middle of the flow path part (20) and provided at a position between the first opening (21*a*) of the first chamber (21) and a connection portion between the tank part (15) and the flow path part (20).

Accordingly, since the second chambers (22) are subjected to the thermal cycle as the first chambers (21), the amount of solution subjected to the thermal cycle can be increased, for example, by two times or more.

For example, the control part (14) may discharge, via the defective chamber, the solution of the second chamber (22) that is connected to the defective chamber via the flow path part (20), and fill the second chamber (22) with the new solution from the tank part (15).

Accordingly, since the second chamber (22) connected to the defective chamber also starts a new thermal cycle with the new solution, for example, a volume of the second chamber (22) may be larger than a volume of the first chamber (21).

Accordingly, the amounts of the solution to be processed and as a result of the process can be greatly increased.

For example, the cartridge (1) may include a plurality of second temperature sensors (27) corresponding to the second chambers (22). The control part (14) may acquire data indicating a temperature from the second temperature sensors (27) in the thermal cycle and manage a temperature of each of the second chambers (27).

Accordingly, the speed and accuracy of temperature control in the thermal cycle can be improved for each of the second chambers (22).

For example, the cartridge (1) may include a heat dissipation fin (34) for cooling the thermal head part (16).

Accordingly, the time required for cooling the first chamber (21) to the target temperature in the thermal cycle can be shortened, the total time required for the thermal cycle can be further shortened.

For example, the cartridge (1) may include a fan (37) for cooling the heat dissipation fin (34).

Accordingly, the cooling efficiency can be improved, and as a result, the total time required for the thermal cycle can be further shortened.

For example, the cartridge (1) may include an electronic cooling element (35) for cooling the heat dissipation fin (34).

Accordingly, the cooling efficiency can be improved, and as a result, the total time required for the thermal cycle can be further shortened.

For example, the cartridge (1) may include a needle-shaped heat conductive member (36) that is inserted at an interface between the tank part (15) and the thermal head part (16) to conduct heat to the heat dissipation fin (34).

Accordingly, the cooling efficiency can be further improved, and as a result, the total time required for the thermal cycle can be greatly shortened.

For example, a cap (10) covering the first chambers (21) may be further included.

Accordingly, it is possible to prevent or suppress natural drying of the solution from the openings of the first chambers (21).

For example, a waste liquid tray (11) receiving the solution discharged from the defective chamber may be further included.

Accordingly, the solution discharged from the defective chamber can be appropriately discarded.

For example, a plate having a plurality of wells may be further included to receive the solution discharged from the first chambers (21) excluding the defective chamber, after completion of a predetermined number of thermal cycles.

Accordingly, the solution of the first chambers (21) which are not defective among the plurality of first chambers (21) can be dispensed into the wells of the plate.

For example, a movement control part moving the cartridge (1) at least one-dimensionally may be further included.

Accordingly, the cartridge (1) can be freely moved. For example, the cartridge (1) can be moved to each of the positions of the cap (10), the waste liquid tray (11), the plate (12), the light source (5), the light receiving sensor (6), etc., which are arranged one-dimensionally.

Further, a nucleic acid amplification method according to an aspect of the disclosure is a nucleic acid amplification method in a microfluidic device, the microfluidic device (100) including a cartridge (1) storing a solution (30) containing a nucleic acid, and a control part (14) controlling the cartridge. The cartridge (1) includes a tank part (15) storing the solution (30), and a plurality of first chambers (21) holding the solution (30) from the tank part (15). In the nucleic acid amplification method, a thermal cycle which changes a temperature of the first chambers (21) is controlled. A number of repetitions of the thermal cycle is counted for each of the first chambers and a count value is stored. A fluorescence intensity of each of the first chambers is acquired for each thermal cycle. It is determined whether the acquired fluorescence intensity of each of the first chambers (21) is within a predetermined range defined in advance for each number of repetitions. The first chamber (21) is determined to be a defective chamber when it is determined that the fluorescence intensity is not within the predetermined range. The count value of the defective chamber is reset, the solution is discharged from the defective chamber, and the defective chamber is filled with a new solution from the tank part.

Accordingly, it is possible to reduce the adverse effect when a quantitative defect or a qualitative defect is present in the starting material contained in the solution held in the first chamber (21). In other words, if a quantitative defect or a qualitative defect is present in the starting material, the control part (14) determines the defective chamber and replaces the solution of the defective chamber with the new solution. That is, the first chamber (21) in which a quantitative defect or a qualitative defect is present in the starting material starts a new thermal cycle with the new solution. Therefore, among the plurality of first chambers (21), the first chambers that have adverse effect can be eliminated or reduced.

It is noted that the reference numerals in parentheses in the above description describe the corresponding components in the embodiment for reference only to facilitate understanding, and the above components are not limited to the referenced components of the embodiment.

In addition, the generally comprehensive or specific embodiments may be realized as systems, methods, integrated circuits, computer programs, recording media such as computer-readable CD-ROMs, etc., or may be realized as any combination of systems, methods, integrated circuits, computer programs, and recording media.

DESCRIPTION OF THE EMBODIMENTS

The disclosure provides a microfluidic device and a nucleic acid amplification method that reduce adverse effects when a starting material is defective.

According to the microfluidic device and the nucleic acid amplification method of the disclosure, it is possible to reduce adverse effects in the presence of a quantitative defect or a qualitative defect in the starting material.

Hereinafter, embodiments of the disclosure will be described in detail with reference to the drawings. The embodiments described below all show comprehensive or specific examples. Numerical values, shapes, materials, components, arrangement positions and connections of the components, steps, the sequence of steps, etc. shown in the following embodiments are merely an example and are not intended to limit the disclosure. Further, among the components in the following embodiments, the components not described in the independent claims will be described as arbitrary components. Each figure does not necessarily show each dimension or each dimension ratio and the like in an exact manner.

EMBODIMENT

Figure 1:
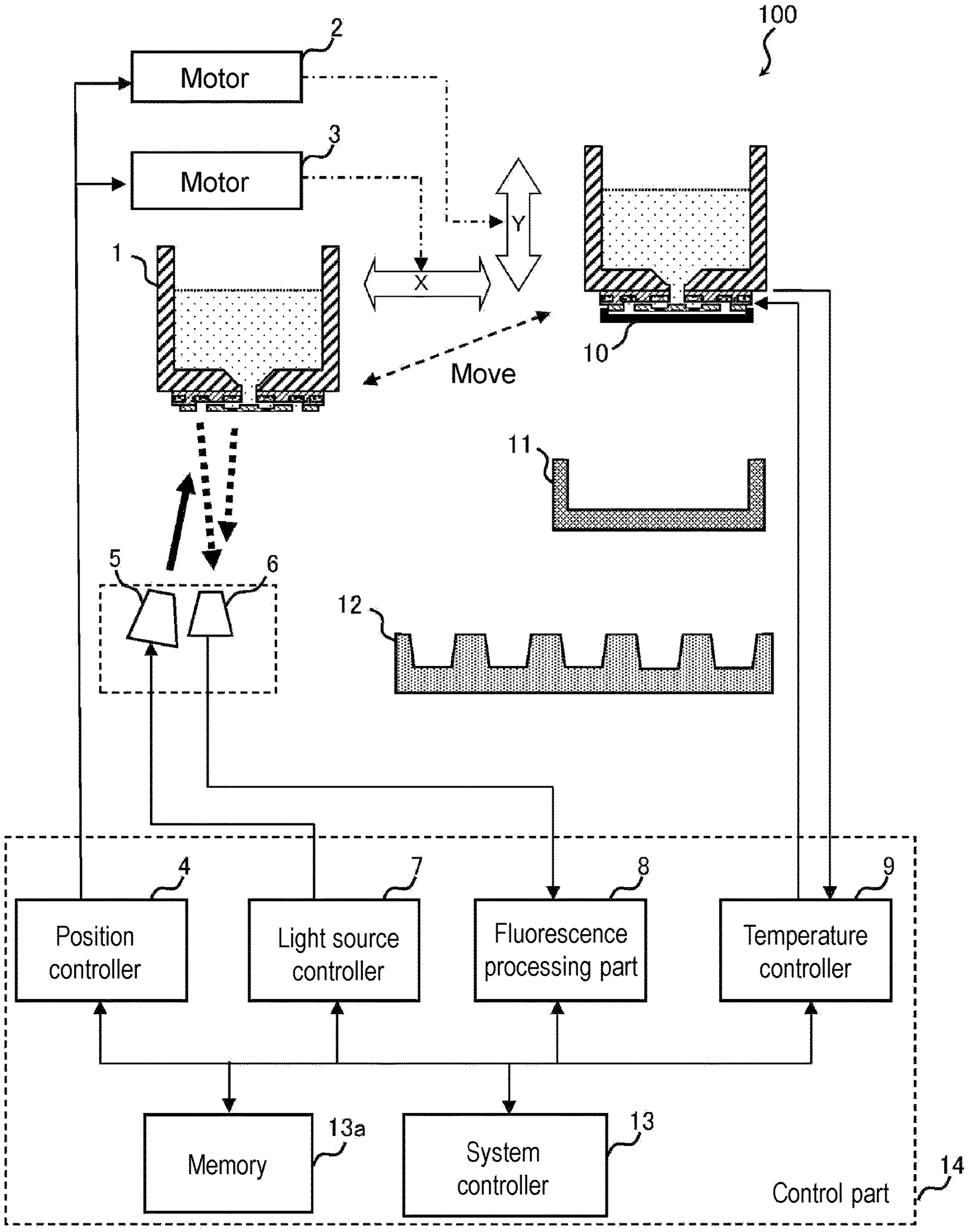
FIG. 1 is a block diagram showing a configuration example of a microfluidic device according to the embodiment.

FIG. 1 is a block diagram showing a configuration example of a microfluidic device 100 according to the embodiment. The microfluidic device 100 in the figure includes a cartridge 1, a motor 2, a motor 3, a position controller 4, a light source 5, a light receiving sensor 6, a light source controller 7, a fluorescence processing part 8, a temperature controller 9, a cap 10, a waste liquid tray 11, a plate 12, a system controller 13, and a control part 14. In the figure, two cartridges 1 are illustrated to show that the cartridge 1 is movable, and it does not mean that two cartridges 1 are present.

The cartridge 1 is a container storing a solution 30 in which a DNA fragment defined as a PCR test target is mixed with a suitable primer and a specific chemical such as an enzyme. The cartridge 1 is configured to be movable at least one-dimensionally (in the X-axis direction). It is movable relative to the mounted plate 12 in the X-Y-axis directions.

Herein, the configuration of the cartridge 1 will be described with reference to FIG. 2.

Figure 2:
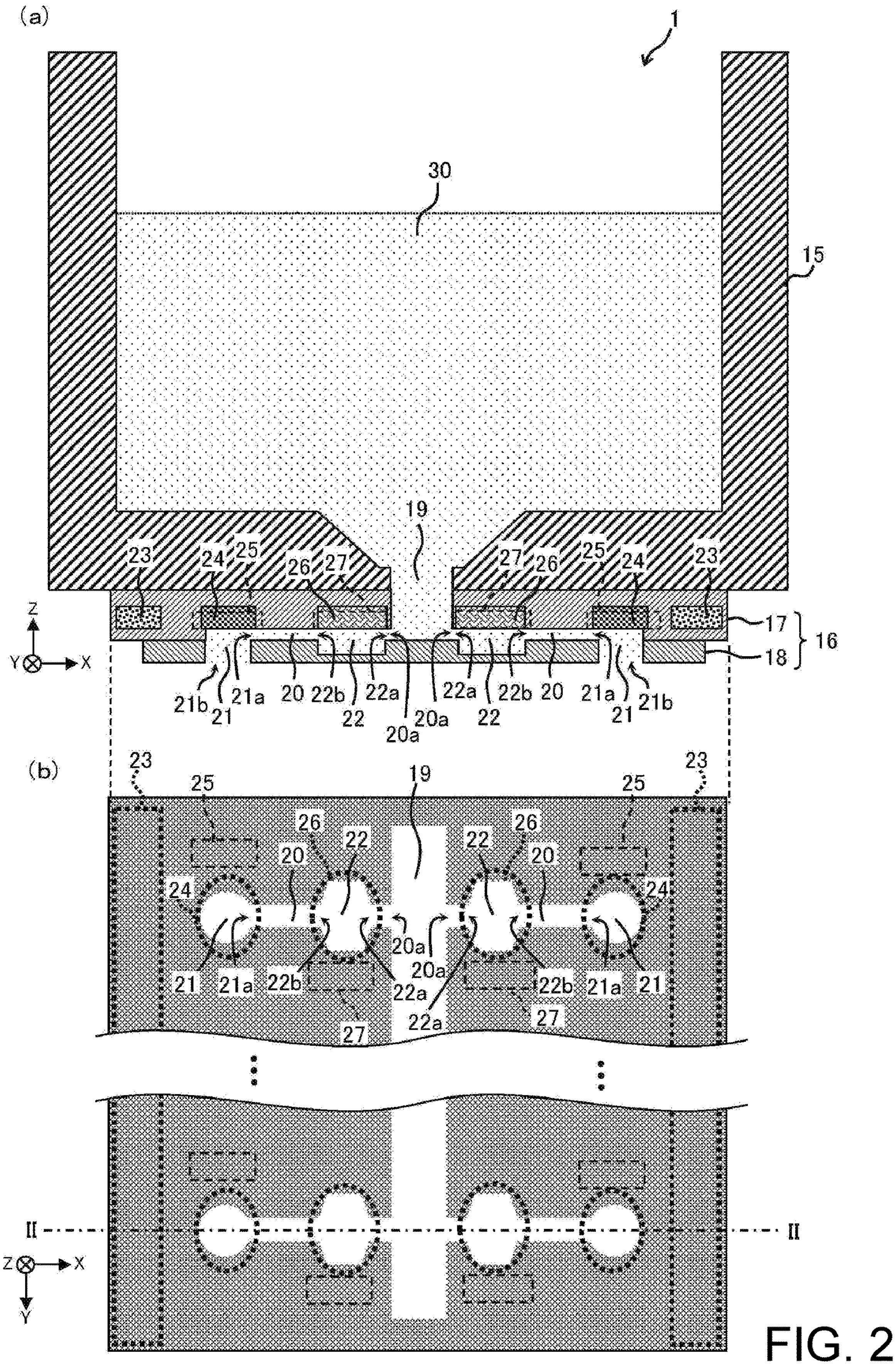
FIG. 2 is a view showing a configuration example of a cross section and a lower surface of a cartridge according to the embodiment.

FIG. 2 is a view showing a configuration example of a cross section and a lower surface of the cartridge 1 according to the embodiment. (a) of the figure is a cross section of the cartridge 1 cut along the X-Z plane, and shows a cross section along line II-II shown in a dot-dash line in (b) of the figure. (b) of the figure shows a cross section cut along the X-Y plane across a flow path part 20 of (a) of the figure.

As shown in FIG. 2, the cartridge 1 includes a tank part 15 and a thermal head part 16.

The tank part 15 has a tank chamber storing the solution 30, and has an opening part 19 connected to the thermal head part 16 on the bottom surface of the tank part 15. The opening part 19 has a strip-shaped elongated rectangular shape extending along the Y axis.

The thermal head part 16 has a semiconductor substrate 17 and a head film 18 bonded to the semiconductor substrate 17. The flow path part 20, a first chamber 21, and a second chamber 22 are formed by a gap formed by bonding the semiconductor substrate 17 and the head film 18 together. The head film 18 may have a property of transmitting irradiation light of the light source 5 and fluorescence of the second chamber 22. In this case, the fluorescence intensity of the second chamber 22 may also be measured.

The flow path part 20 connects the opening part 19 of the tank part 15 and the first chamber 21. One end of the flow path part 20 is a third opening **20*a* connected to the opening part 19. Another end of the flow path part 20 is connected to a first opening 21*a* of the first chamber 21. Further, in the middle of the flow path part 20, the second chamber 22** is provided by enlarging the cross-sectional area of the flow path.

The first chamber 21 holds the solution 30 that flows in from the tank part 15 via the opening part 19 and the flow path part 20. The first chamber 21 has a first opening **21*a*** connected to the flow path part 20 and a second opening 21*b* exposed on the lower surface. The second opening 21*b* is also a discharge nozzle.

The second chamber 22 holds the solution 30 flowing in from the tank part 15 via the opening part 19. The second chamber 22 is provided in the middle of the flow path part 20 and also functions as a flow path for carrying the solution 30 to the first chamber 21. The second chamber 22 has a fourth opening 22*a* through which the solution 30 flows in from the tank part 15, and a fifth opening 22*b* through which the solution 30 flows out to the first chamber 21 side. The total number of the first chambers 21 included in the cartridge 1 depends on the size of the cartridge 1, but may be, for example, about 32 to 640.

The semiconductor substrate 17 includes a substrate heater 23, a first heater 24, a first temperature sensor 25, a second heater 26, and a second temperature sensor 27.

The substrate heater 23 heats the semiconductor substrate 17 under the control of the temperature controller 9. In the example of the figure, the substrate heater 23 is a strip-shaped elongated resistor arranged on two sides of the semiconductor substrate 17 along the Y direction.

The first heater 24 is provided adjacent to the first chamber 21 in the Z direction and heats the solution 30 of the first chamber 21 under the control of the temperature controller 9.

The first temperature sensor 25 is arranged adjacent to or immediately proximate the first chamber 21 in the −Y direction to detect the temperature of the solution 30 held in the first chamber 21 and notify it to the temperature controller 9.

The second heater 26 is provided adjacent to the second chamber 22 in the Z direction and heats the solution 30 of the second chamber 22 under the control of the temperature controller 9.

The second temperature sensor 27 is arranged adjacent to or immediately proximate the second chamber 22 in the Y direction to detect the temperature of the solution 30 held in the second chamber 22 and notify it to the temperature controller 9.

Next, returning to FIG. 1, the configuration of the cartridge 1 will be described.

The motor 2 moves the cartridge 1 in the Y direction.

The motor 3 moves the cartridge 1 in the X direction.

The position controller 4 controls the motor 2 and the motor 3 to move the cartridge 1 to arbitrary positions in the X direction and the Y direction.

The light source 5 irradiates light to the first chamber 21 or the second chamber 22. The peak wavelength of the light source is, for example, 488 nm. The solution 30 may be stained in advance with a fluorescent substance so as to fluoresce when irradiated with light. The wavelength of the fluorescence is, for example, 522 nm.

The light receiving sensor 6 measures the fluorescence intensity of the first chamber 21 or the second chamber 22 and notifies it to the fluorescence processing part 8. The light source 5 and the light receiving sensor 6 are formed as one unit and are movable relative to the cartridge 1.

The light source controller 7 controls the light source 5 to irradiate the first chamber 21 or the second chamber 22 for each thermal cycle. It performs control of measuring the fluorescence intensity.

The fluorescence processing part 8 performs control of measuring the fluorescence intensity of the first chamber 21 or the second chamber 22 for each thermal cycle.

In the thermal cycle, the temperature controller 9 sequentially performs, for example, steps in stages of (a) denaturation reaction, (b) annealing, and (c) extension reaction. The temperature controller 9 heats the first chamber 21 by heating of the heater in stages (a) and (c). In the transition from (a) to (b), heat dissipation is performed by natural heat dissipation or attaching a heat dissipation material to the cartridge 1. Alternatively, forced cooling is performed by an electronic cooling element or air blowing. The denaturation reaction of (a) is continued at 95° C. for 1 minute. The annealing of (b) is continued at 40° C. to 55° C. for 1 minute. The extension reaction of (c) is continued at 72° C. for 1 minute. The time and temperature for continuing each stage of (a), (b) and (c) may be appropriately set depending on the target nucleic acid, and the concentration and type of the solution.

The cap 10 prevents or suppresses the solution 30 held in the first chamber 21 from evaporating from the second opening 21*b* and drying out.

The waste liquid tray 11 receives the solution 30 discharged from the first chamber 21 having defective fluorescence, as a result of the fluorescence intensity measurement for each thermal cycle.

The plate 12 receives the solution of which the thermal cycle has been completed for a predetermined number of times and the amplification of the DNA fragment has reached the plateau region. The plate 12 has a plurality of wells.

The system controller 13 controls the position controller 4, the light source controller 7, the fluorescence processing part 8, and the temperature controller 9.

A memory 13*a* stores a program executed by a CPU serving as the system controller 13 and various data. As the various data, the memory 13*a* may store, for example, a predetermined reference range for each number of thermal cycle repetitions, a count value which is the number of individual thermal cycle repetitions for the first chamber 21, a fluorescence intensity corresponding to the individual count value of the first chamber 21, and values of NG_flag indicating whether the individual count value and fluorescence intensity of the first chamber 21 is defective.

The control part 14 includes the position controller 4, the light source controller 7, the fluorescence processing part 8, the temperature controller 9, and the memory 13*a*.

Next, dimension examples of the flow path part 20, the first chamber 21, and the second chamber 22 of the cartridge 1 will be described.

Figure 3:
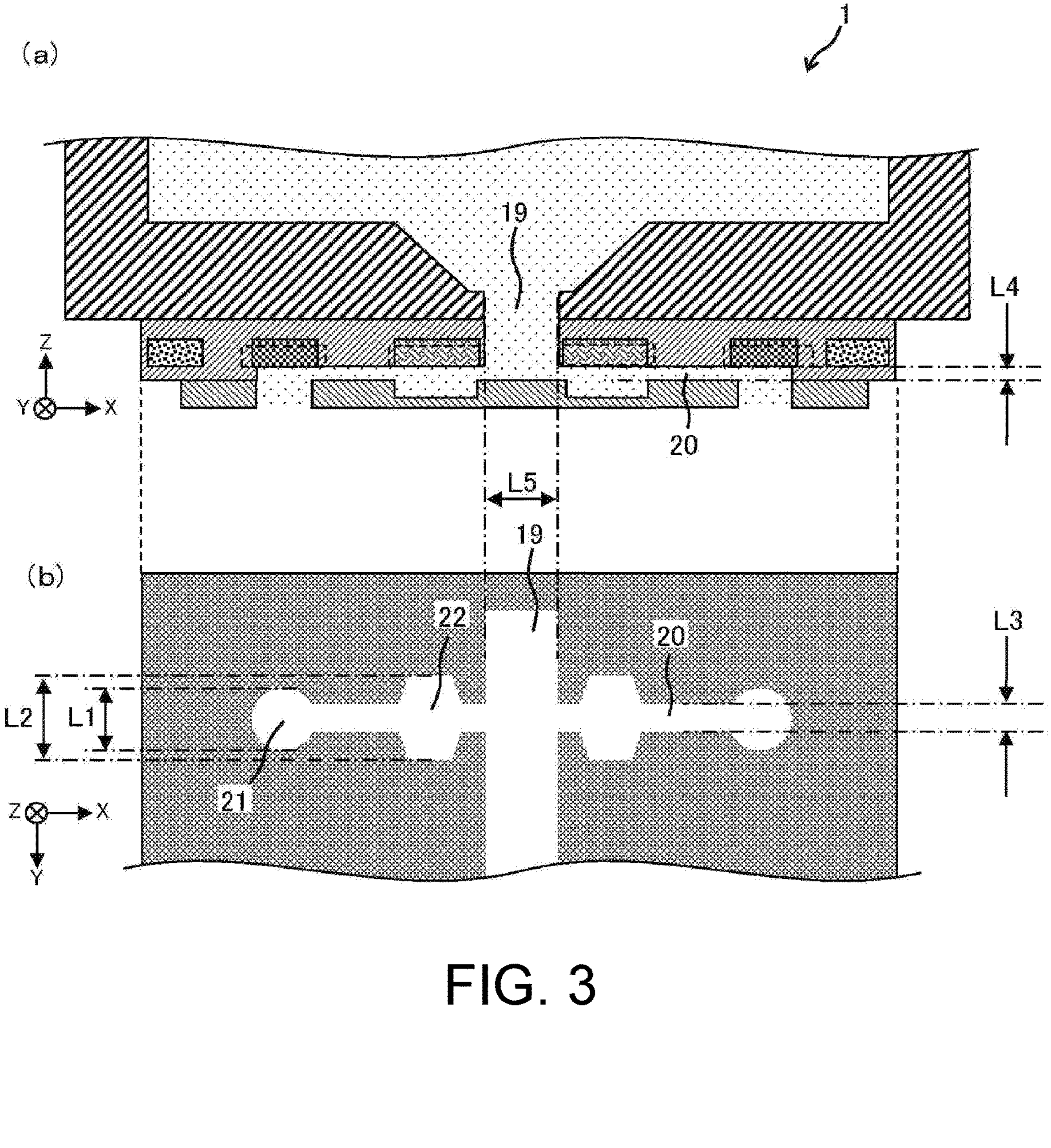
FIG. 3 is a view showing a dimension example of the cartridge according to the embodiment.

FIG. 3 is a view showing a dimension example of the cartridge 1 according to the embodiment. FIG. 3 shows only a main part of FIG. 2.

A dimension L1 in FIG. 3 indicates the diameter of the first chamber 21 which is circular in a plan view viewed in the Z direction. The dimension L1 may be tens of micrometers (μm), for example, 40 μm.

A dimension L2 indicates the length in the Y direction of the hexagonal second chamber 22 in a plan view viewed in the Z direction. The dimension L2 may be tens of micrometers (μm), for example, 50 μm. In the figure, the volume of the second chamber 22 is larger than the volume of the first chamber 21.

A dimension L3 indicates the width of the flow path part 20 in the Y direction. The flow path part 20 may allow the solution 30 to flow, and the dimension L3 may be a value smaller than the dimension L1 and the dimension L2, and may be, for example, 35 μm.

A dimension L4 indicates the width of the flow path part 20 in the Z direction. The flow path part 20 may allow the solution 30 to flow. The dimension L4 may be a value smaller than the dimension L1 and the dimension L2, and may be, for example, 18 μm.

A dimension L5 indicates the width of the opening part 19. The dimension L5 may be tens to hundreds of micrometers (μm), and may be, for example, 240 μm.

The solution 30 is a mixture of a target DNA fragment with a fluorescent dye (e.g., SYBR (registered trademark) Green), a primer, a DNA polymerase, and a buffer. When the solution 30 is injected into the tank part 15, the solution 30 is filled in the portion from the flow path part 20 to the second chamber 22 and the first chamber 21 via the opening part 19.

The above dimensions should be designed to meet the following. When the solution 30 is filled from the tank part 15 to the opening part 19, the flow path part 20, the second chamber 22, and the first chamber 21, the air pressure is balanced so that the solution 30 does not fall naturally from the opening of the first chamber 21 serving as a discharge nozzle in the −Z direction.

Figure 4:
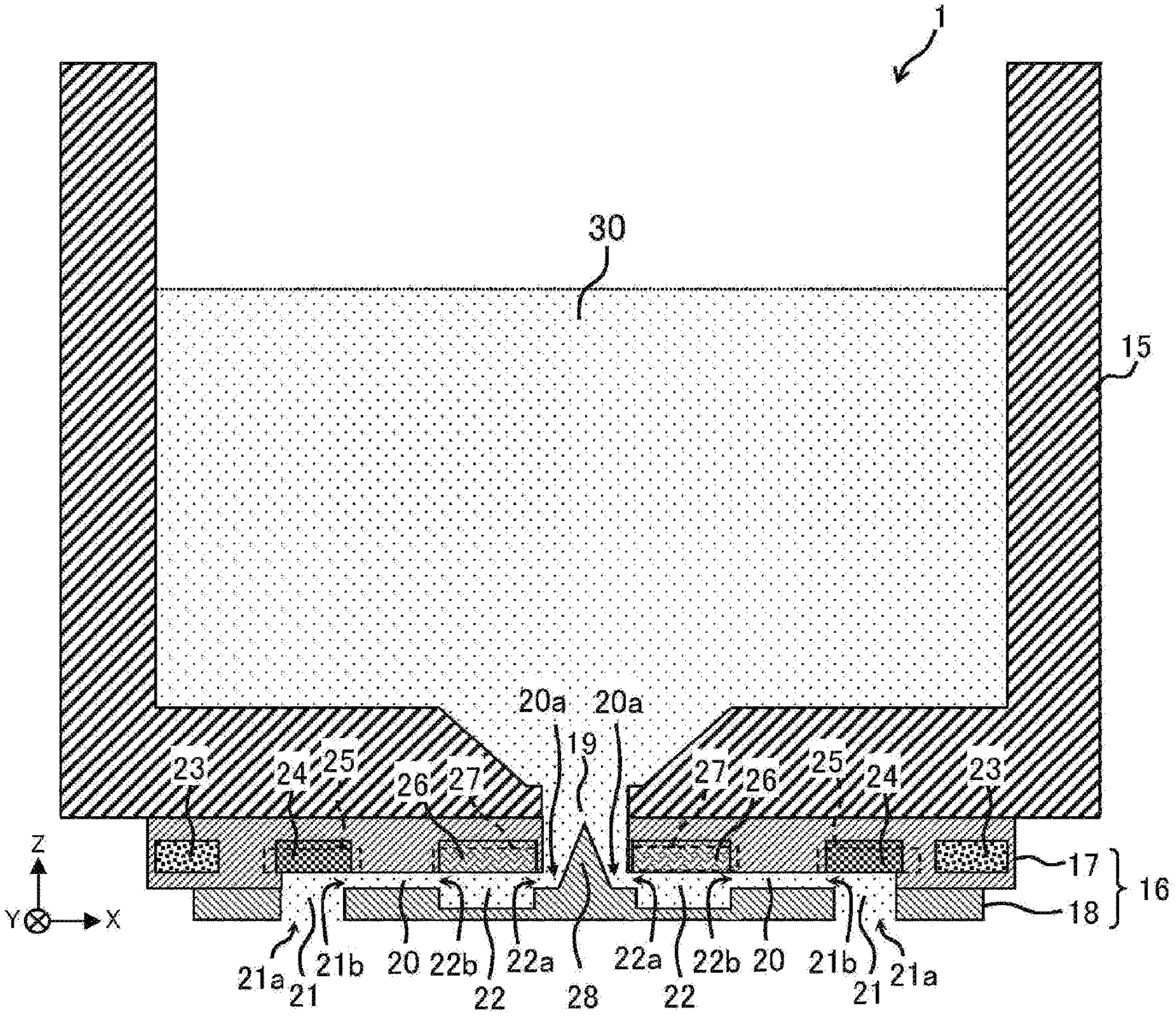
FIG. 4 is a view showing a configuration of a cross section and a lower surface of the cartridge according to a first modification example of the embodiment.

The cross section of the cartridge 1 shown in (a) of FIG. 2 may also be as shown in FIG. 4. FIG. 4 is a view showing a configuration of a cross section and a lower surface of the cartridge 1 according to a first modification example of the embodiment. Compared to FIG. 2, in FIG. 4, a partition wall 28 is added to the head film 18. Accordingly, the heat insulating property is improved between the two second chambers 22 sandwiching the partition wall 28, and adverse thermal effect can be suppressed.

Next, the circuit configuration of the cartridge 1 will be described.

Figure 5:
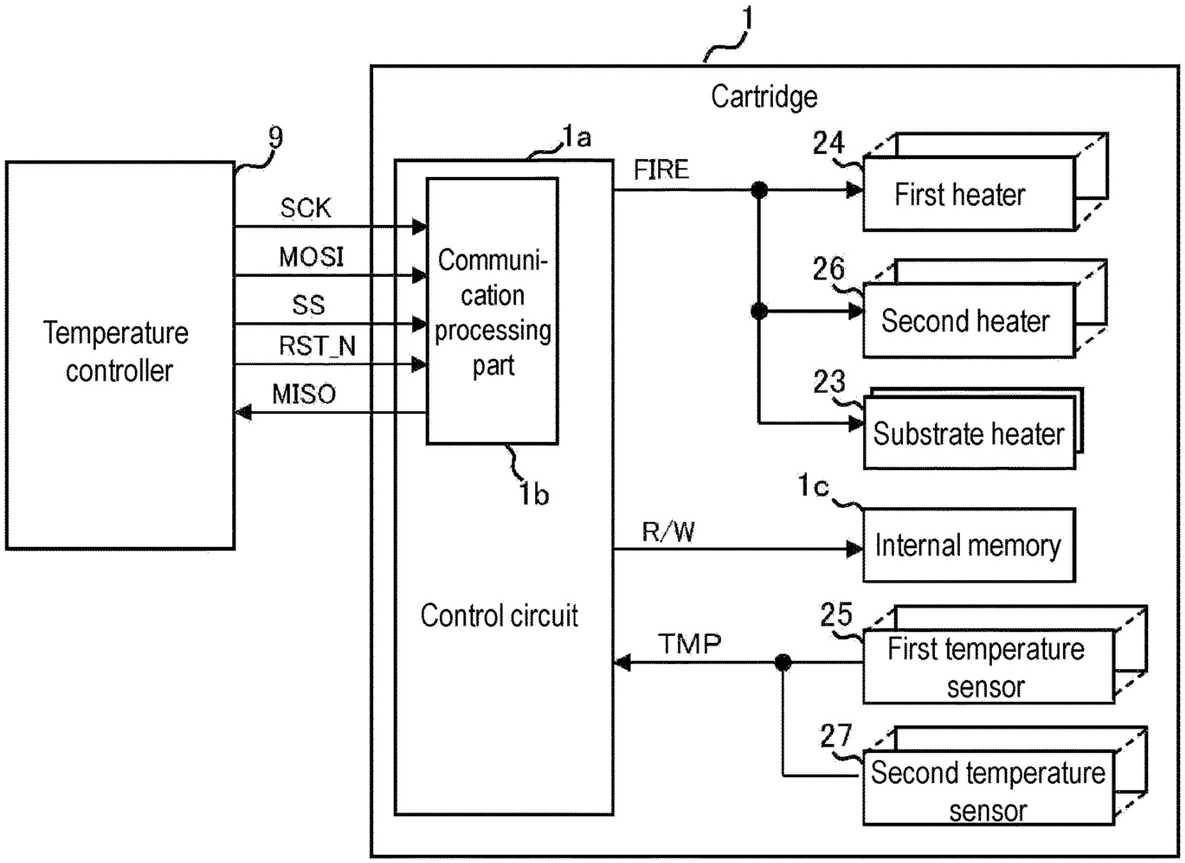
FIG. 5 is a block diagram showing a circuit configuration example of the cartridge according to the embodiment.

FIG. 5 is a block diagram showing a circuit configuration example of the cartridge 1 according to the embodiment. The figure also shows the temperature controller 9 and signal lines connected with the temperature controller 9. As shown in the figure, the cartridge 1 includes a control circuit 1*a*, a plurality of first heaters 24, a plurality of second heaters 26, a plurality of substrate heaters 23, an internal memory 1*c*, a plurality of first temperature sensors 25, and a plurality of second temperature sensors 27.

The control circuit 1*a* includes therein a communication processing part 1*b*.

The communication processing part 1*b* is connected to the temperature controller 9 by a Serial Peripheral Interface (SPI). SCK is an abbreviation for Serial Clock, which is a clock signal. MOSI is an abbreviation for Master Out Slave In, and is an address, command, data, etc. sent as serial data from the temperature controller 9 to the communication processing part 1*b*. SS is an abbreviation for Slave Select and is a chip select signal. RST N is a reset signal. MISO is an abbreviation for Master In Slave Out, and is serial data from the communication processing part 1*b* to the temperature controller 9. The communication processing part 1*b* receives, from the temperature controller 9, a command for instructing heating of the first heaters 24, the second heaters 26, and the substrate heaters 23 individually or in groups, a command for instructing discharge, and the like. Further, the communication processing part 1*b* receives a request for temperature data for the first temperature sensors 25 and the second temperature sensors 27 individually or in groups, and transmits the requested temperature data to the temperature controller 9.

When the communication processing part 1*b* receives a command instructing heating, the control circuit 1*a* controls the corresponding first heaters 24, second heaters 26, and substrate heaters 23 to heat or discharge according to the command. Further, when the communication processing part 1*b* receives a command requesting temperature data, the control circuit 1*a* performs control so that temperature data is acquired from the corresponding first temperature sensors 25 and second temperature sensors 27, the acquired temperature data is stored in the internal memory 1*c*, and further, the temperature data is transmitted to the temperature controller 9 via the communication processing part 1*b* according to the command. FIRE in the figure is a signal instructing heat generation. R/W is a signal instructing reading/writing of the internal memory 1*c*. TMP is a signal indicating the temperature data.

The communication between the temperature controller 9 and the communication processing part 1*b* is not limited to SPI, and may be another communication method.

Next, the heating operation and the discharge operation by the first chamber 21 and the first heater 24 will be described.

Figure 6:
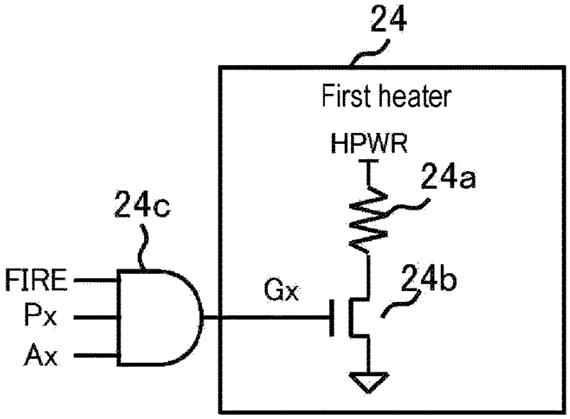
FIG. 6 is a circuit diagram showing a configuration example of the first heater and its periphery according to the embodiment.

FIG. 6 is a circuit diagram showing a configuration example of the first heater 24 and its periphery according to the embodiment. As shown in the figure, the first heater 24 has a heater resistor 24*a* and a switch transistor 24*b*. The heater resistor 24*a* generates heat when the switch transistor 24*b* is on. The switch transistor 24*b* is in an on state when a gate signal Gx is at a high level and is in an off state when the gate signal Gx is at a low level.

An address decoder 24*c* is a circuit in the control circuit 1*a*, decodes an address signal Ax and an address signal Px which indicates a group, and instructs a target first heater 24 for heating or discharging. Each of the address signal Ax and the address signal Px is actually a multi-bit signal, but are shown in the figure as 1-bit signals for the sake of simplicity.

Figure 7:
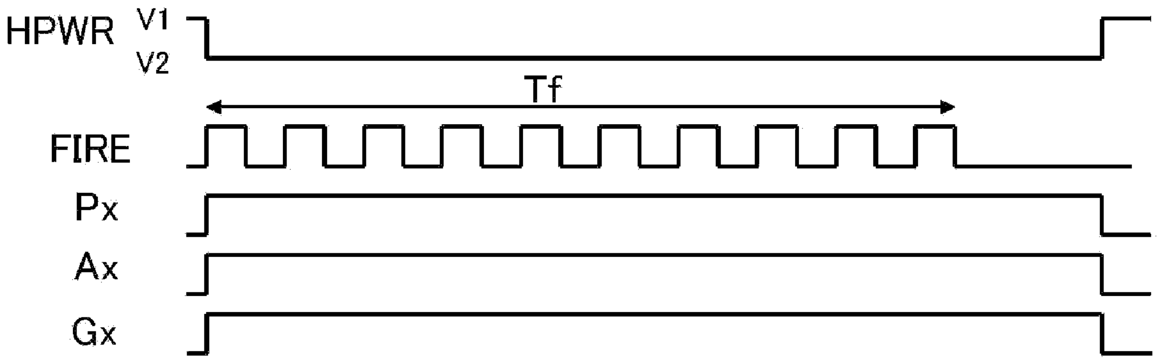
FIG. 7 is a time chart showing an operation example of heating the solution of the first chamber according to the embodiment.

FIG. 7 is a time chart showing an operation example of heating the solution of the first chamber 21 according to the embodiment. The figure shows a heating operation example in the first heater 24 corresponding to the address signal Ax and the address signal Px. In the heating operation, a power supply voltage HPWR of the heater resistor 24*a* drops from a high voltage V1 to a low voltage V2, and the FIRE signal becomes a plurality of intermittent pulse signals. The heater resistor 24*a* generates heat intermittently according to the pulse. Accordingly, the first heater 24 heats the solution of the first chamber 21 without discharging it. In the heating operation, for example, V2 of the power supply voltage HPWR may be 4 V, and a period Tf of the intermittent pulse may be about 500 microseconds (μs). In the heating operation, the temperature controller 9 performs feedback control that repeats the heating operation and the temperature acquisition.

Figure 8:
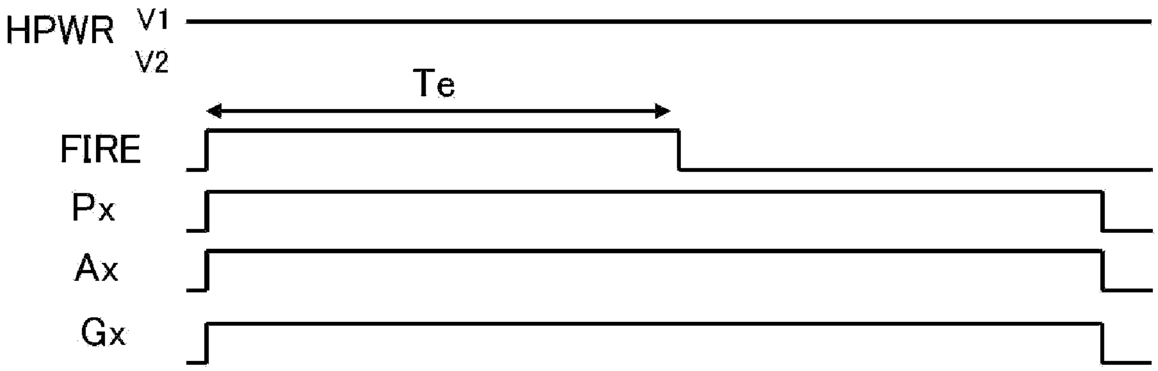
FIG. 8 is a time chart showing an operation example of discharging the solution of the first chamber according to the embodiment.

FIG. 8 is a time chart showing an operation example of discharging the solution of the first chamber 21 according to the embodiment. In the discharge operation of the figure, the power supply voltage HPWR of the heater resistor 24*a* is maintained at the high voltage V1, and the FIRE signal has one pulse having a long high level period. Accordingly, the heater resistor 24*a* generates more heat than in FIG. 7. As a result, the first heater 24 generates bubbles in the solution of the first chamber 21 to discharge the solution. In the discharge operation, for example, V1 of the power supply voltage HP WR may be 10 V, and a period Te of the pulse for maintaining the high level may be about 100 μs.

Next, the changes in position by the movement of the cartridge 1 in the microfluidic device 100 will be described.

Figure 9:
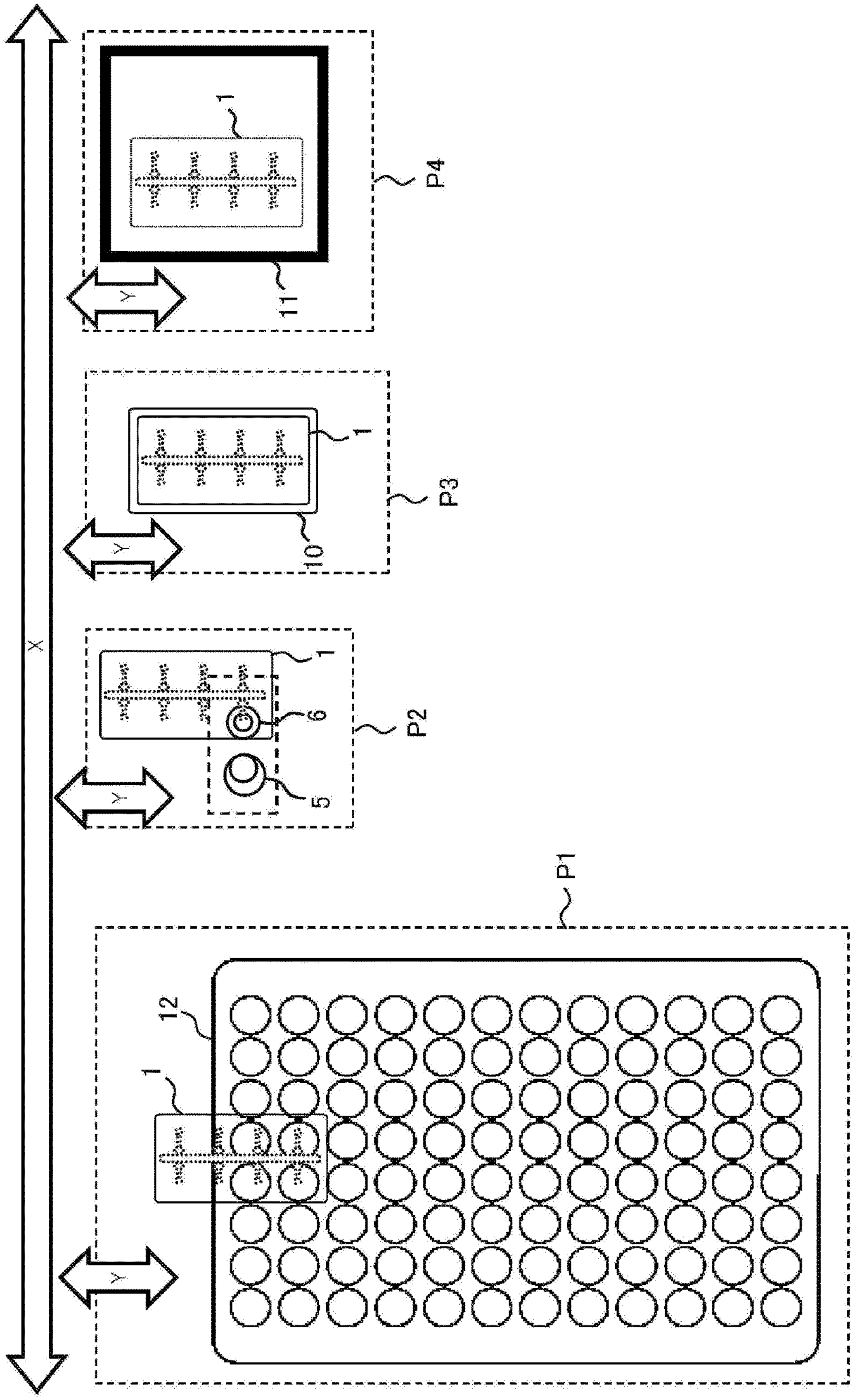
FIG. 9 is a view showing positions of moving destinations of the cartridge according to the embodiment.

FIG. 9 is a view showing positions of moving destinations of the cartridge 1 according to the embodiment. In the figure, a position P1 indicates the position of the plate 12. A position P2 indicates the position of the optical part composed of the light source 5 and the light receiving sensor 6. A position P3 indicates the position of the cap 10. A position P4 indicates the position of the waste liquid tray 11. The position controller 4 selectively moves the cartridge 1 to these positions.

When repetitions of the thermal cycle have been completed, i.e., when the amplification of the DNA fragment is in the plateau state, the position controller 4 moves the cartridge 1 to the position P1 to dispense the solution 30 held in the first chambers 21 and the second chambers 22. Further, by finely adjusting the position at the position P1, the position controller 4 moves the discharge target, i.e., the first chamber 21 or the second chamber 22, to the position of each well in the plate 12. Accordingly, the required amount of the solution 30 can be dispensed into each well from the first chambers 21 and the second chambers 22.

To measure the fluorescence intensity for each thermal cycle, the position controller 4 moves the cartridge 1 to the position P2 to measure the fluorescence intensity of the first chamber 21. At this time, the fluorescence intensity of the second chamber 22 may also be measured. When the irradiation range of the light source 5 extends to both the first chamber 21 and the second chamber 22, the position controller 4 may have the combined fluorescence intensity of the first chamber 21 and the second chamber 22 measured.

The position controller 4 moves the cartridge 1 to the position P3 and attaches the cap 10 while the cartridge 1 is in the thermal cycle. This prevents or suppresses drying of the first chamber 21.

Further, in the measurement of the fluorescence intensity for each thermal cycle, when a defective first chamber 21 is present, the position controller 4 moves the cartridge 1 to the position P4 to replace the solution 30 of the first chamber 21 by discharging the solution 30 of the first chamber 21 to the waste liquid tray 11.

Next, the overall flow of the nucleic acid amplification operation in the microfluidic device 100 will be described.

Figure 10:
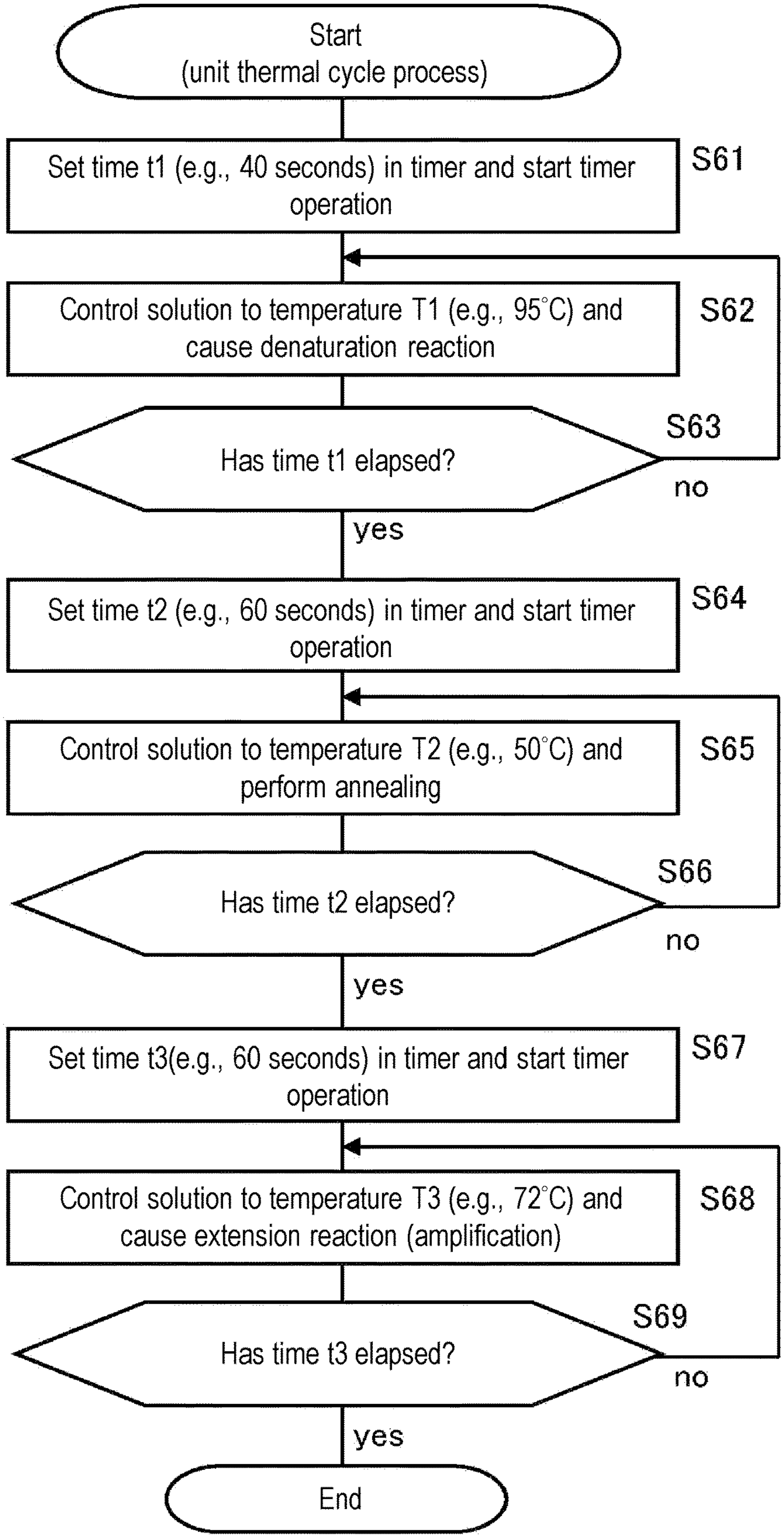
FIG. 10 is a flowchart showing a unit thermal cycle process in FIG. 11.
Figure 11:
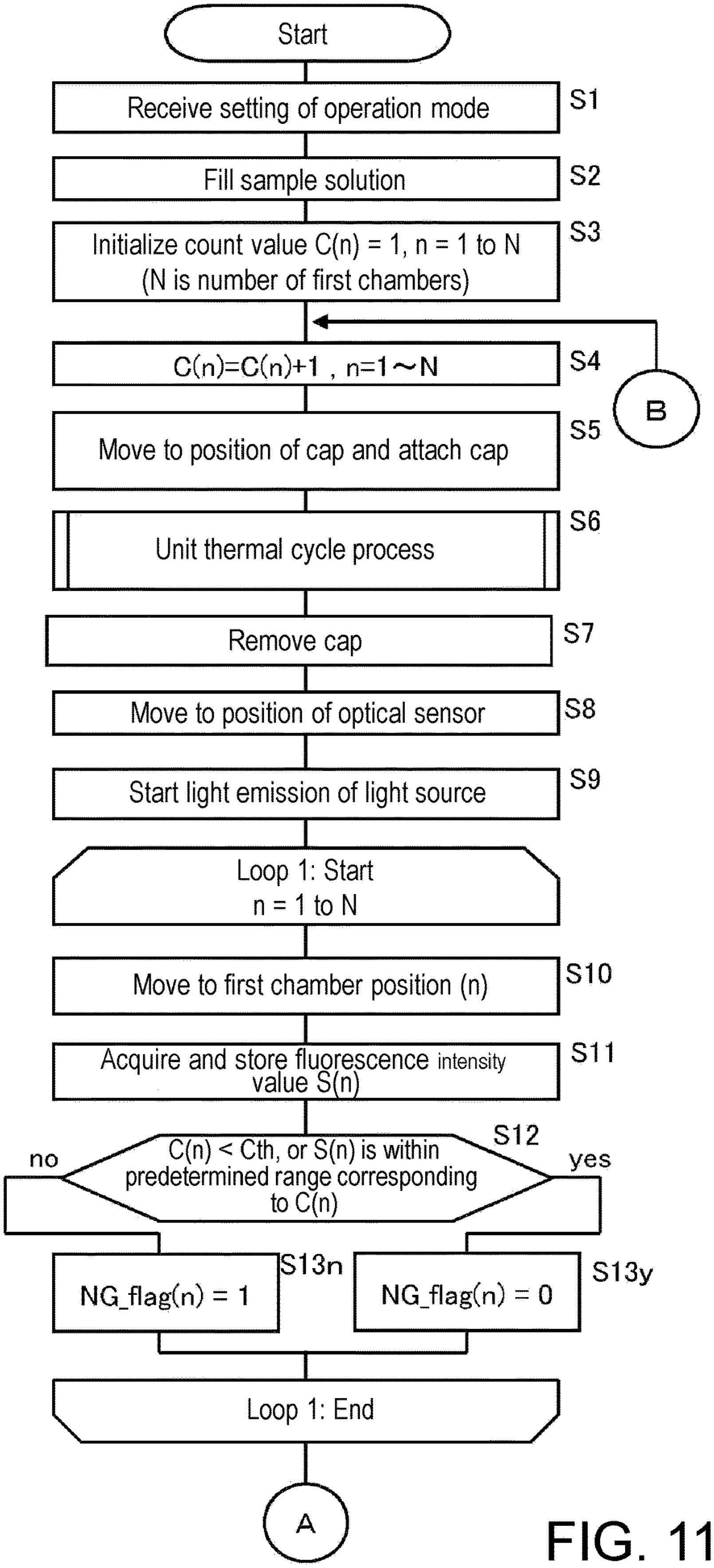
FIG. 11 is a flowchart showing an operation for nucleic acid amplification using the microfluidic device according to the embodiment.
Figure 12:
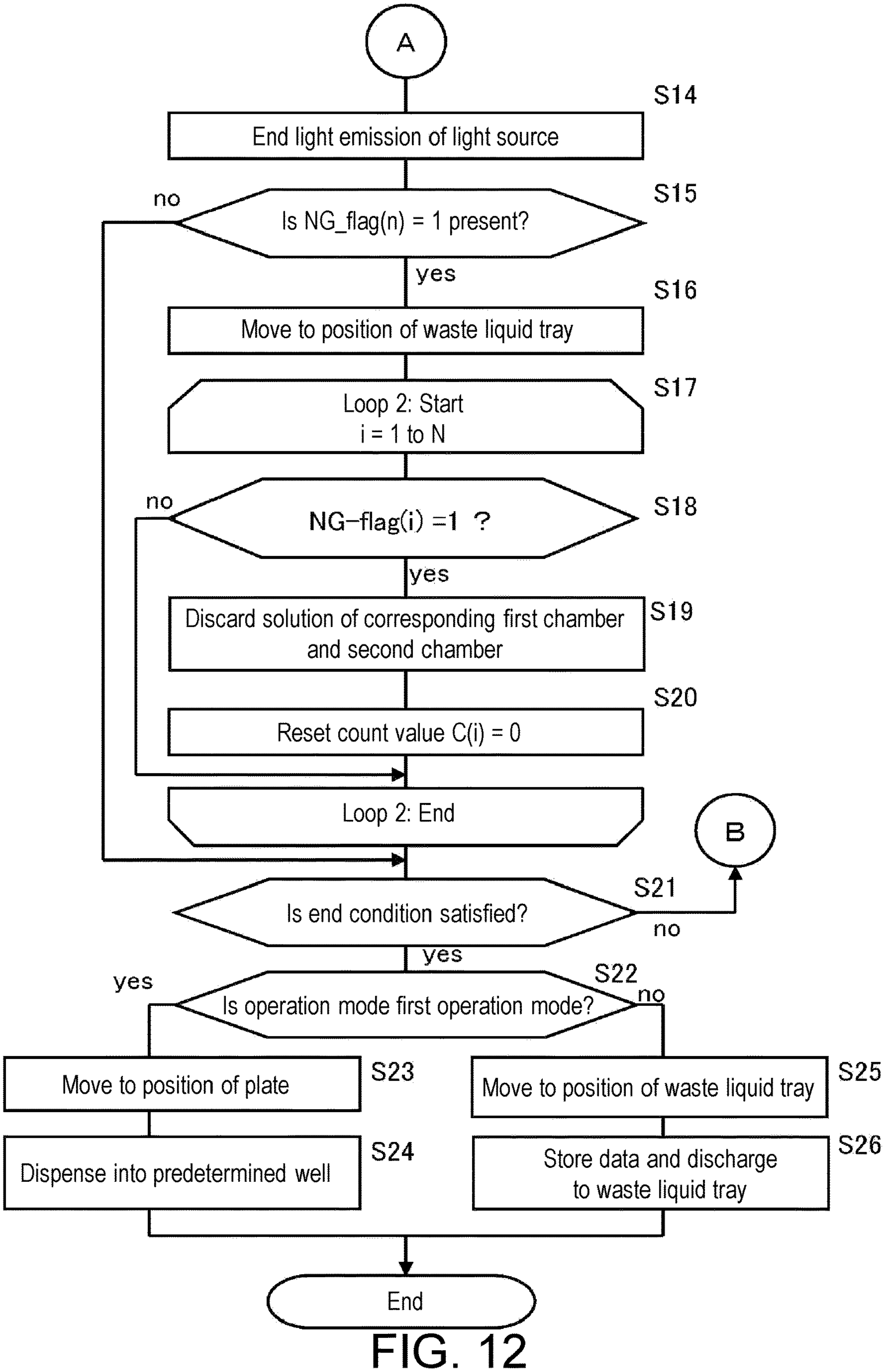
FIG. 12 is a flowchart showing a continuation of the operation of FIG. 11.

FIG. 11 is a flowchart showing an operation for nucleic acid amplification using the microfluidic device 100 according to the embodiment. FIG. 12 is a flowchart showing a continuation of the operation of FIG. 11. Further, FIG. 10 is a flowchart showing an example of a unit thermal cycle process in FIG. 11.

First, an example of a unit thermal cycle process of FIG. 10 will be described.

As shown in FIG. 10, in the unit thermal cycle process, the control part 14 first sets a time t1 in an internal timer and starts a timer operation (S61). The time t1 is, for example, 40 seconds. The control part 14 controls the held solution 30 to a temperature T1 and causes a denaturation reaction for each of the first chambers 21 and the second chambers 22 (S62). The temperature T1 is, for example, 95° C. Further, the control part 14 determines whether the time t1 has elapsed from the start of the timer operation (S63). If the time t1 has not elapsed, the process returns to step S62, and if the time t1 has elapsed, the process proceeds to step S64. Steps S61 through S63 give rise to a denaturation reaction, which is the first stage of the unit thermal cycle.

Further, the control part 14 first sets a time t2 in the internal timer and starts the timer operation (S64). The time t2 is, for example, 60 seconds. The control part 14 controls the held solution 30 to a temperature T2 and performs annealing for each of the first chambers 21 and the second chambers 22 (S65). The temperature T2 is, for example, 50° C. Further, the control part 14 determines whether the time t2 has elapsed from the start of the timer operation (S66). If the time t2 has not elapsed, the process returns to step S65, and if the time t2 has elapsed, the process proceeds to step S67. Steps S64 through S66 are annealing, which is the second stage of the unit thermal cycle.

Next, the control part 14 first sets a time t3 in the internal timer and starts the timer operation (S67). The time t3 is, for example, 60 seconds. The control part 14 controls the held solution 30 to a temperature T3 and performs an extension reaction, i.e., amplification, for each of the first chambers 21 and the second chambers 22 (S68). The temperature T3 is, for example, 72° C. Further, the control part 14 determines whether the time t3 has elapsed from the start of the timer operation (S69). If the time t3 has not elapsed, the process returns to step S68, and if the time t3 has elapsed, the unit thermal cycle process is completed. Steps S67 through S69 cause an extension reaction, which is the third stage of the unit thermal cycle.

Next, an example of the nucleic acid amplification operation will be described with reference to FIG. 11 and FIG. 12. The nucleic acid amplification operation includes so-called qPCR, and further includes a process of suppressing adverse effects when the starting material is defective.

In FIG. 11, the control part 14 first receives an operation mode of the microfluidic device 100 (S1). In this example, either a first operation mode or a second operation mode is received as the operation mode according to a user operation. The first operation mode is an operation mode in which the solution 30 containing the DNA fragment amplified by the nucleic acid amplification operation of FIG. 11 and FIG. 12 is dispensed into the plate 12. The second operation mode is an operation mode in which the solution 30 containing the DNA fragment amplified by the nucleic acid amplification operation of FIG. 11 and FIG. 12 is discarded and only the data obtained by qPCR is stored. For example, the user may select the second operation mode if qPCR may achieve the objectives of analysis and identification of the test target, and may select the first operation mode to further utilize the solution 30 amplified by qPCR.

Further, the user fills the tank part 15 with the sample solution 30 (S2). The solution 30 contains the target DNA fragment, a fluorescent dye (e.g., SYBR Green), a primer, a DNA polymerase, and a buffer. When the solution 30 is injected into the tank part 15, the solution 30 is filled in the portion from the flow path part 20 to the second chamber 22 and the first chamber 21 via the opening part 19.

Up to this point is the user preparatory stage of the nucleic acid amplification operation. After the preparatory stage, the control part 14 initializes a count value C(n) to 1 for each first chamber 21 (S3). n is the total number of first chambers 21 included in the cartridge 1. n is, for example, about 32 to 640. Further, the count value C(n) indicates a count value which is the number of repetitions of the thermal cycle of the corresponding first chamber 21.

Further, the control part 14 increments the count value C(n) by 1 for all n of n=1 to N (S4), and moves the cartridge 1 to the position P3 of the cap 10 and attaches the cap 10 (S5). In this state, the control part 14 performs the unit thermal cycle process shown in FIG. 10 (S6).

After the unit thermal cycle process is completed, the control part 14 removes the cap 10 from the cartridge 1 (S7), moves to the position P2 of the optical part composed of the light source 5 and the light receiving sensor 6 (S8), and starts light emission of the light source 5 (S9).

In this state, the control part 14 measures and stores the fluorescence intensity for each of the N first chambers 21 and checks for defects (loop 1).

In the loop 1, the control part 14 moves the optical part to a first chamber 21 position (n) corresponding to n (S10), and measures the fluorescence intensity with the light receiving sensor 6. The control part 14 acquires a measured fluorescence intensity value S(n) and stores it in the memory 13*a* (S11). Further, when C(n) is smaller than a predetermined threshold value Cth, the control part 14 proceeds to S13*y* regardless of the fluorescence intensity value S(n), and when C(n) is equal to or greater than the predetermined threshold value Cth, the control part 14 determines whether the fluorescence intensity value S(n) is within a predetermined range defined in advance associated with the number of repetitions (S12).

Herein, the predetermined range indicates a range of the expected value for each number of repetitions calculated from the data of the known PCR amplification effect for the known DNA fragment in the solution 30. Therefore, S12 is a step of determining whether the known DNA fragment is amplified as expected from the data. Accordingly, when the fluorescence intensity value S(n) is within the predetermined range, it means that a quantitative defect or a qualitative defect is not present in the starting material of the solution 30.

In contrast, when the fluorescence intensity value S(n) is not within the predetermined range, it means that there is a high possibility that a quantitative defect or a qualitative defect of the starting material of the solution 30 has occurred. When the fluorescence intensity value S(n) is not within the predetermined range, the corresponding first chamber 21 is referred to as a defective chamber.

When C(n) is smaller than the predetermined threshold value Cth in S12, the control part 14 sets NG_flag(n)=0 (513*y*). The predetermined threshold value Cth is, for example, about 10 to 20. When the number of repetitions is equal to or less than the threshold value Cth, the fluorescence intensity is small and there is no significant difference due to the number of repetitions, so NG_flag(n)=0 is forcibly set.

The control part 14 sets NG_flag(n)=0 when C(n) is equal to or greater than the predetermined threshold value Cth, and the fluorescence intensity value S(n) is within a predetermined range defined in advance associated with the number of repetitions (513*y*).

The control part 14 sets NG_flag(n)=1 when C(n) is equal to or greater than the predetermined threshold value Cth, and the fluorescence intensity value S(n) is not within the predetermined range defined in advance associated with the number of repetitions (S13*n*).

The control part 14 executes the loop 1 process for the N first chambers 21 corresponding to n=1 to N.

The NG_flag(n) is stored in the memory 13*a* in association with the count value C(n).

Next, as shown in FIG. 12, the control part 14 ends the light emission of the light source 5 after the loop 1 process is completed (S14), and determines whether NG_flag(n)=1 stored in the memory 13*a* is present (S15). The control part 14 proceeds to S21 when NG_flag(n)=1 is not present, and proceeds to S16 when NG_flag(n)=1 is present.

Further, the control part 14 moves the cartridge 1 to the position P4 of the waste liquid tray 11 (S16). In this state, the control part 14 executes a loop 2 process (S17).

The control part 14 determines whether NG_flag(i)=1 in the loop 2 process (S18). When the control part 14 determines that NG_flag(i)=1 (yes in S18), the solution held in the corresponding first chamber 21 and second chamber 22 is discarded (S19). In S19, the control part 14 causes the first chamber 21 to perform a plurality of discharge operations. The total of the solution 30 in the first chamber 21, the solution 30 in the second chamber 22, and the solution 30 in the flow path part 20 is discharged to the waste liquid tray 11 by the discharge operations. Further, by this discharge, the first chamber 21, the second chamber 22, and the flow path part 20 are filled with the new solution 30 from the tank part 15.

Next, the control part 14 resets a value C(i) corresponding to the first chamber 21 to 0 (S20).

In the loop 2 process, for all defective chambers corresponding to NG_flag(n)=1, the solution of the corresponding second chamber 22 and the flow path part 20 may also be replaced with the new solution 30 to newly start the nucleic acid amplification operation.

After the end of the loop 2 process, the control part 14 determines, for example, whether the current state satisfies an end condition (S21). Herein, the end condition may be one or more of the following: the amplification of nucleic acid is in the plateau state and is stagnant; the average of the fluorescence intensity S(n) has reached the threshold value; the number of times of executions of the unit thermal cycle process reaches a number of times obtained by adding a margin number of times to a predetermined number of times corresponding to the plateau state. The control part 14 proceeds to S4 when determining that the end condition is not satisfied, and proceeds to S22 when determining that the end condition is satisfied.

Further, the control part 14 determines whether the operation mode is the first operation mode (S22).

When it is determined to be the first operation mode, the control part 14 moves the cartridge 1 to the position P1 of the plate 12 (S23), and dispenses the solution 30 from the cartridge 1 into predetermined wells of the plate 12 (S24). The dispensed plate 12 is further subjected to other tests such as electrophoresis.

In contrast, when it is determined not to be the first operation mode, the control part 14 moves the cartridge 1 to the position P4 of the waste liquid tray 11 (S25), stores data such as the count value C(n) and the fluorescence intensity value S(n) in the memory 13*a*, and discharges the solution 30 to the waste liquid tray 11 (S26). In the discharge in S26, at least the solution 30 in the first chamber 21, the second chamber 22, and the flow path part 20 may be discharged.

In the nucleic acid amplification operation of FIG. 11 and FIG. 12, it is possible to reduce the adverse effect when a quantitative defect or a qualitative defect is present in the starting material contained in the solution 30 held in the first chamber 21. In other words, if a quantitative defect or a qualitative defect is present in the starting material, the control part 14 determines the defective chamber and replaces the solution 30 of the defective chamber with the new solution. That is, the first chamber 21 in which a quantitative defect or a qualitative defect is present in the starting material starts a new thermal cycle with the new solution. Therefore, among the plurality of first chambers 21, the first chambers that have adverse effect can be eliminated or reduced.

Further, since one first heater 24 corresponds to one first chamber 21, in the thermal cycle, the time required to heat the first chamber 21 to the target temperature can be shortened, and the total time required for the thermal cycle can be shortened.

Similarly, since one second heater 26 corresponds to one second chamber 22, in the thermal cycle, the time required to heat the second chamber 22 to the target temperature can be shortened, and the total time required for the thermal cycle can be shortened.

Further, since the first temperature sensor 25 is provided for each first chamber 21, the speed and accuracy of temperature control in the thermal cycle can be improved.

Similarly, since the second temperature sensor 27 is provided for each second chamber 22, the speed and accuracy of temperature control in the thermal cycle can be improved.

Further, since the substrate heater 23 is provided, for example, the semiconductor substrate 17 can be auxiliary heated when the environment temperature is low.

Further, in the above embodiment, it has been shown as an example that, in order to set the solution 30 to the target temperature, heating is actively performed by heaters, and cooling is performed by natural cooling. However, the cooling may also be performed by active cooling instead of natural cooling. Next, a configuration example of actively cooling the solution will be described.

Figure 13:
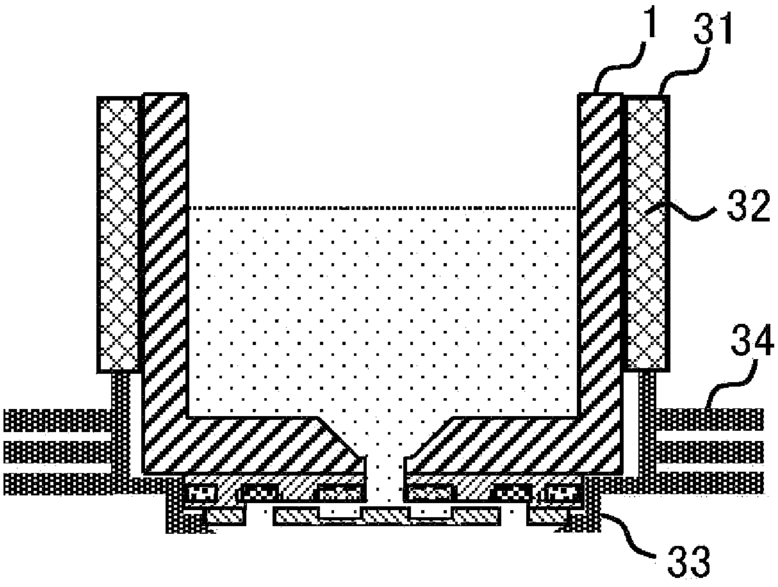
FIG. 13 is a view showing a cross-sectional configuration example of the cartridge according to a second modification example of the embodiment.

FIG. 13 is a view showing a cross-sectional configuration example of the cartridge 1 according to a second modification example of the embodiment. The figure shows a configuration example in which the cartridge 1 is held by a cartridge holder 31 in order to enhance the cooling function for the solution 30 in the cartridge 1.

The cartridge holder 31 includes a sidewall 32, a heat dissipation plate 33, and a heat dissipation fin 34.

The sidewall 32 holds the tank part 15 of the cartridge 1.

The heat dissipation plate 33 is in contact with the lower part of the tank part 15 of the cartridge 1, the semiconductor substrate 17, and the head film 18, and conducts the heat of the cartridge 1 to the heat dissipation fin 34.

The heat dissipation fin 34 dissipates heat conducted from the heat dissipation plate 33.

According to this configuration, compared to natural cooling without the heat dissipation fin 34, in a unit thermal cycle process, the time required for cooling the first chamber 21 to the target temperature can be shortened, and the total time required for the unit thermal cycle process can be further shortened.

Figure 14:
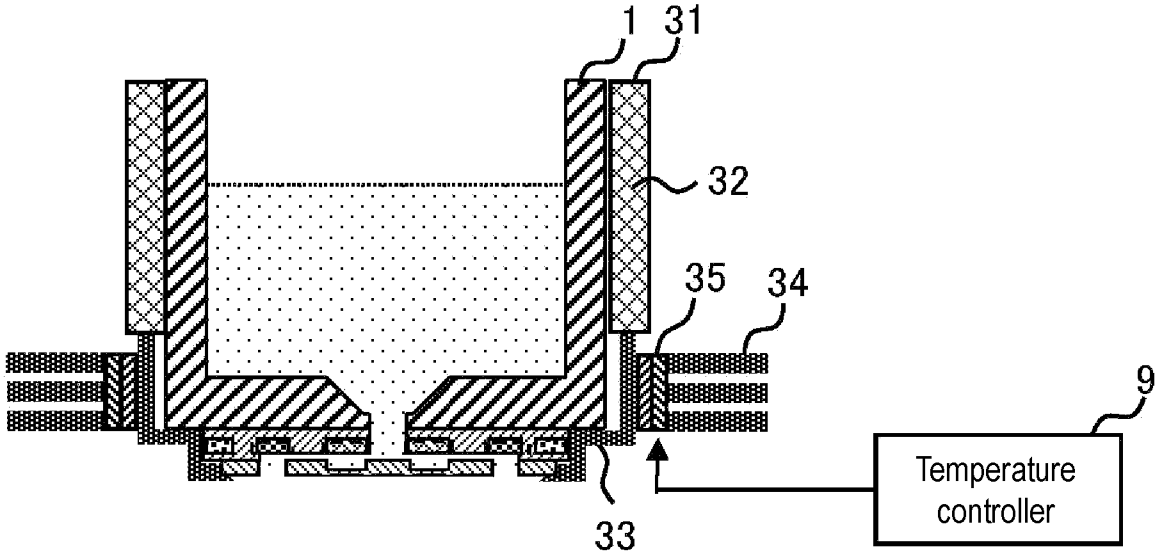
FIG. 14 is a view showing a cross-sectional configuration example of the cartridge according to a third modification example of the embodiment.

FIG. 14 is a view showing a cross-sectional configuration example of the cartridge 1 according to a third modification example of the embodiment. FIG. 14 is different from FIG. 13 in that an electronic cooling element 35 is sandwiched at an interface at which the heat dissipation plate 33 and the heat dissipation fin 34 face each other and are connected to each other.

The electronic cooling element 35 is, for example, a Peltier element, a cooling element having a semiconductor heterostructure, or the like. The Peltier element has two planar electrodes, and transfers heat to the planar electrode on the heat dissipation plate 33 side or the planar electrode on the heat dissipation fin 34 side. Further, the cooling element having a semiconductor heterostructure is an element that has a $GaAs/Al_xGa_{1-x}As$ heterostructure and cools by the resonant tunneling effect and thermionic emission. The cooling capacity of the electronic cooling element 35 may be controlled by the control of the temperature controller 9.

Accordingly, the configuration of FIG. 14 has a higher cooling capacity than that of FIG. 13. The total time required for the unit thermal cycle process can be further shortened. The electronic cooling element 35 may also be a cooling element different from the Peltier element and the cooling element having a semiconductor heterostructure.

Figure 15:
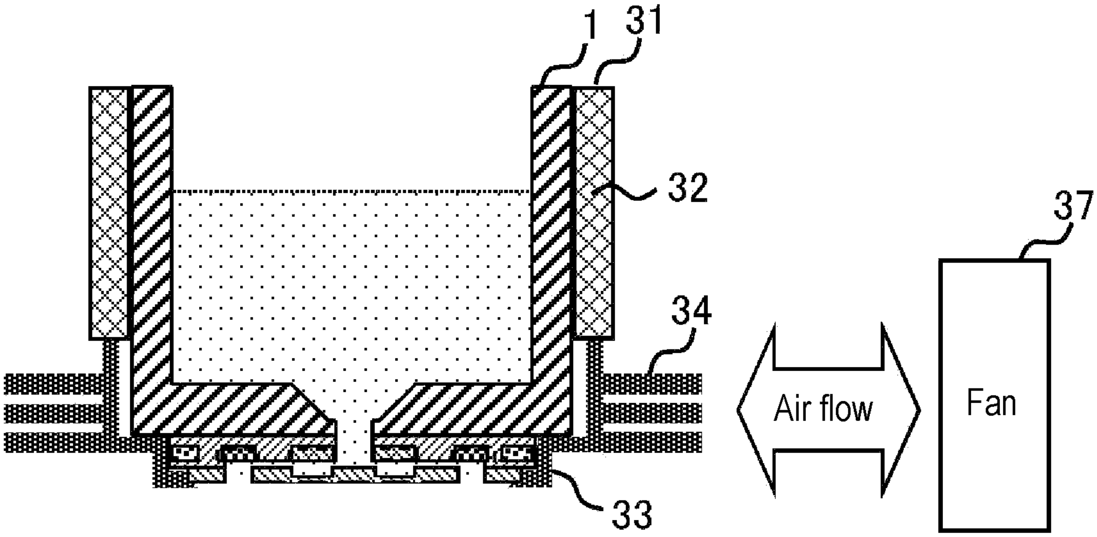
FIG. 15 is a view showing a cross-sectional configuration example of the cartridge according to a fourth modification example of the embodiment.

FIG. 15 is a view showing a cross-sectional configuration example of the cartridge 1 according to a fourth modification example of the embodiment. FIG. 15 is different from FIG. 13 in that it includes a fan 37. The fan 37 blows air to the heat dissipation fin 34 or takes in air from the heat dissipation fin 34.

Accordingly, the configuration of FIG. 15 has a higher cooling capacity than that of FIG. 13. The total time required for the unit thermal cycle process can be further shortened.

Figure 16:
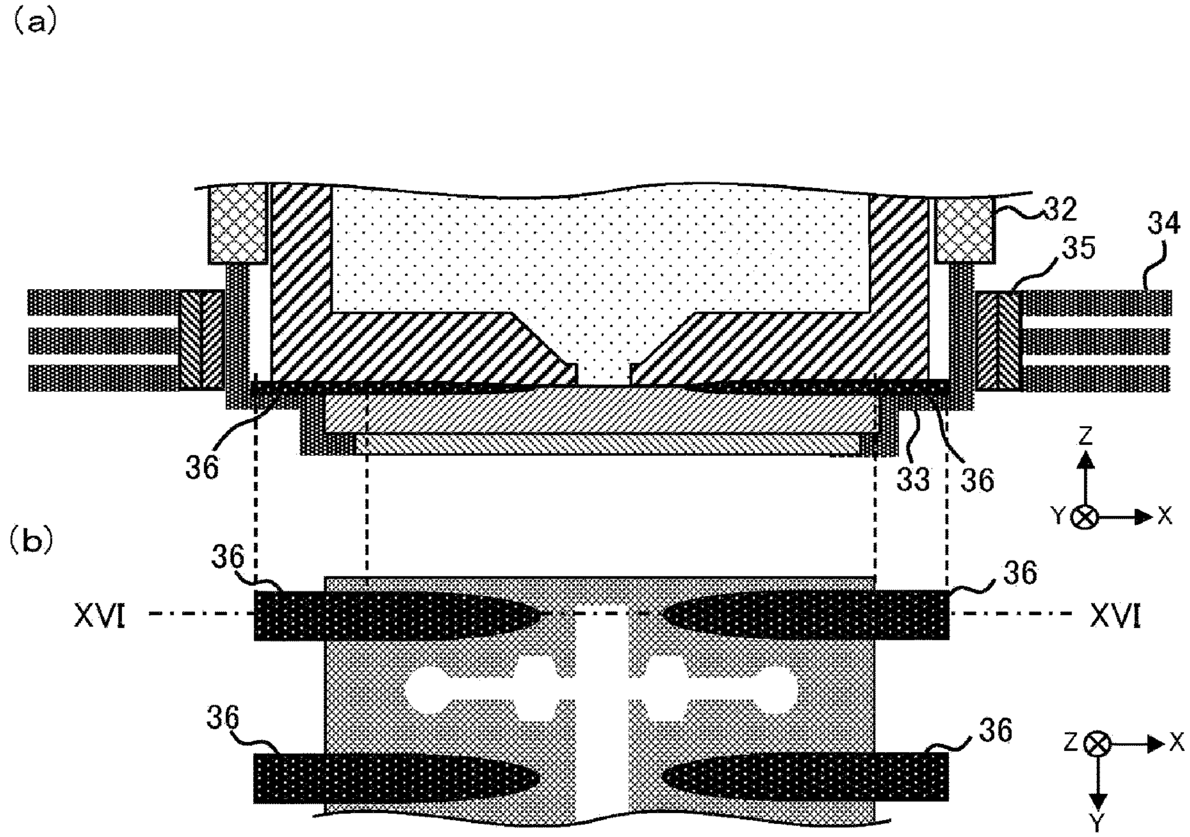
FIG. 16 is a view showing a configuration example of a cross section and a lower surface of the cartridge according to a fifth modification example of the embodiment.

FIG. 16 is a view showing a configuration example of a cross section and a lower surface of the cartridge 1 according to a fifth modification example of the embodiment. FIG. 16 is different from FIG. 14 in that a heat conductive member 36 is added.

The heat conductive member 36 is a needle-shaped member that is inserted at an interface between the tank part 15 and the thermal head part 16 and conducts heat to the heat dissipation fin 34, and is in contact with the heat dissipation plate 33.

Accordingly, the configuration of FIG. 16 has a higher cooling capacity than that of FIG. 14. The total time required for the unit thermal cycle process can be further shortened.

Although FIG. 13 to FIG. 16 have shown configuration examples in which the cartridge 1 and the cartridge holder 31 are separate bodies, the cartridge holder 31 may also be integrally formed with the cartridge 1. Further, the heat dissipation fin 34 may also be integrally formed with the cartridge 1. Similarly, the electronic cooling element 35 may also be integrally formed with the cartridge 1.

In each of the above embodiments, each component may be configured with dedicated hardware or may be realized by executing a software program suitable for each component. Each component may be realized by a program execution part such as a CPU or a processor which reads and executes a software program recorded on a recording medium such as a hard disk or a semiconductor memory.

Although the microfluidic device 100 and the nucleic acid amplification method according to the embodiment of the disclosure have been described above, the disclosure is not limited to the above embodiment.

Further, specifically, each of the above devices may be configured as a computer system composed of a microprocessor, a ROM, a RAM, a hard disk drive, a display unit, a keyboard, a mouse, and the like. Computer programs are stored in the RAM or the hard disk drive. Each device achieves its function by operation of the microprocessor according to the computer program. Herein, the computer program is configured by combining a plurality of instruction codes indicating commands to a computer in order to achieve a predetermined function.

Further, some or all of the components that form each of the above devices may be composed of one system LSI (large-scale integration). A system LSI is a super-multifunctional LSI manufactured by integrating a plurality of components on one chip, and, for example, includes a computer system configured to include a microprocessor, a ROM, a RAM, and the like. In this case, the computer program is stored in the ROM. The system LSI achieves its function by operation of the microprocessor according to the computer program.

Furthermore, some or all of the components forming each of the above devices may be composed of an IC card or a separate module that may be attached to and detached from each device. The IC card or the module is a computer system composed of a microprocessor, a ROM, a RAM, and the like. The IC card or the module may include the above super-multifunctional LSI. The IC card or the module achieves its function by operation of the microprocessor according to the computer program. The IC card or the module may have tamper resistance.

Further, the disclosure may be the methods shown above. Further, the disclosure may be computer programs that realize these methods by a computer, or may be digital signals composed of the above computer programs.

Further, the disclosure may record the above computer program or the above digital signal to a non-transitory computer-readable recording medium, such as a flexible disk, a hard disk, a CD-ROM, an MO, a DVD, a DVD-ROM, a DVD-RAM, a BD (Blu-ray (registered trademark)) disc, a semiconductor memory, or the like. Further, it may be the digital signal recorded on these non-transitory recording media.

Further, the disclosure may transmit the computer program or the digital signal via a telecommunication line, a wireless or wired communication line, a network represented by the Internet, data broadcasting, or the like.

Further, the disclosure may be a computer system including a microprocessor and a memory, the memory may store the above computer program, and the microprocessor may operate according to the computer program.

Further, by recording the programs or the digital signals on the non-transitory recording medium and transferring the same, or by transferring the programs or the digital signals via the network or the like, they may be executed by another independent computer system.

Further, the above embodiment and the above modification examples may be combined with each other.

The disclosure may be used in devices that amplify nucleic acids.

What is claimed is:

1. A microfluidic device for amplifying a nucleic acid, comprising:
- a cartridge; and
- a control part controlling the cartridge,
- wherein the cartridge comprises
  - (i) a tank part storing a solution containing the nucleic acid;
  - (ii) a plurality of first chambers holding the solution from the tank part;
  - (iii) a plurality of first heaters corresponding to the plurality of first chambers; and
  - (iv) a plurality of flow path parts connecting the tank part and the plurality of first chambers, and
  - each of the plurality of first chambers comprises (a) a first opening connected to one of the plurality of flow path parts; and
    - (b) a second opening for discharging the solution held in each of the plurality of first chambers, the second opening exposed on a lower surface of each of the plurality of first chambers, and
- the control part is configured to:
  - control execution of a thermal cycle which changes a temperature of the first chambers,
  - count a number of repetitions of the thermal cycle for each of the first chambers and store a count value,
  - acquire a fluorescence intensity of each of the first chambers for each thermal cycle,
  - determine whether the acquired fluorescence intensity of each of the first chambers is within a predetermined range defined in advance for each number of repetitions,
  - determine one of the first chambers to be a defective chamber when it is determined that the fluorescence intensity is not within the predetermined range, and
  - reset the count value of the defective chamber, generate a bubble in the solution in the defective chamber by one of the plurality of first heaters corresponding to the defective chamber, discharge the solution from the defective chamber via the second opening by generation of the bubble, and fill the defective chamber with the solution containing the nucleic acid stored in the tank part via one of the plurality of flow path parts and the first opening.

2. The microfluidic device according to claim 1, wherein the cartridge comprises a plurality of first temperature sensors corresponding to the plurality of first chambers, and
- the control part acquires data indicating a temperature from the plurality of first temperature sensors during the thermal cycle and manages a temperature of each of the plurality of first chambers.

3. The microfluidic device according to claim 1, wherein the cartridge comprises a thermal head part,
- the thermal head part comprises a semiconductor substrate and a head film bonded to the semiconductor substrate,
- the semiconductor substrate comprises one of the plurality of first heaters and one of the plurality of flow path parts, and
- each of the first chambers and each of the flow path parts are formed as a gap formed by bonding the semiconductor substrate and the head film together.

4. The microfluidic device according to claim 3, wherein the semiconductor substrate comprises a substrate heater.

5. The microfluidic device according to claim 3, wherein the cartridge comprises a heat dissipation fin for cooling the thermal head part.

6. The microfluidic device according to claim 5, wherein the cartridge comprises a fan for cooling the heat dissipation fin.

7. The microfluidic device according to claim 5, wherein the cartridge comprises an electronic cooling element for cooling the heat dissipation fin.

8. The microfluidic device according to claim 5, wherein the cartridge comprises a needle-shaped heat conductive member that is inserted at an interface between the tank part and the thermal head part to conduct heat to the heat dissipation fin.

9. The microfluidic device according to claim 1, further comprising a cap covering the plurality of first chambers.

10. The microfluidic device according to claim 1, further comprising a waste liquid tray receiving the solution discharged from the defective chamber.

11. A microfluidic device for amplifying a nucleic acid, comprising:
- a cartridge; and
- a control part controlling the cartridge,
- wherein the cartridge comprises:
  - a tank part storing a solution containing the nucleic acid; and
  - a plurality of first chambers holding the solution from the tank part, and the control part is configured to:
  - control execution of a thermal cycle which changes a temperature of the first chambers,
  - count a number of repetitions of the thermal cycle for each of the first chambers and store a count value,
  - acquire a fluorescence intensity of each of the first chambers for each thermal cycle,
  - determine whether the acquired fluorescence intensity of each of the first chambers is within a predetermined range defined in advance for each number of repetitions,
  - determine one of the first chambers to be a defective chamber when it is determined that the fluorescence intensity is not within the predetermined range, and
  - reset the count value of the defective chamber, discharge the solution from the defective chamber, and fill the defective chamber with the solution containing the nucleic acid stored in the tank part, the microfluidic device further comprising a plate having a plurality of wells that receive the solution discharged from the plurality of first chambers excluding the defective chamber, after completion of a predetermined number of thermal cycles.

12. A nucleic acid amplification method in a microfluidic device, the microfluidic device comprising:

a cartridge storing a solution containing a nucleic acid; and a control part controlling the cartridge, wherein the cartridge comprises:

a tank part storing the solution; and a plurality of first chambers holding the solution from the tank part, and the nucleic acid amplification method comprises:

controlling a thermal cycle which changes a temperature of the first chambers;

counting a number of repetitions of the thermal cycle for each of the first chambers and storing a count value;

acquiring a fluorescence intensity of each of the first chambers for each thermal cycle;

determining whether the acquired fluorescence intensity of each of the first chambers is within a predetermined range defined in advance for each number of repetitions;

determining the first chamber to be a defective chamber when it is determined that the fluorescence intensity is not within the predetermined range; and resetting the count value of the defective chamber, discharging the solution from the defective chamber, and filling the defective chamber with a new solution from the tank part.

* * * * *